(12) United States Patent
Mohamadi

(10) Patent No.: US 9,372,256 B2
(45) Date of Patent: Jun. 21, 2016

(54) WAFER SCALE SENSOR ULTRA-WIDEBAND ARRAY FOR TISSUE DIAGNOSIS

(71) Applicant: Farrokh Mohamadi, Irvine, CA (US)

(72) Inventor: Farrokh Mohamadi, Irvine, CA (US)

(73) Assignee: Farrokh Mohamadi, Irvine, CA (US)

( * ) Notice: Subject to any disclaimer, the term of this patent is extended or adjusted under 35 U.S.C. 154(b) by 340 days.

(21) Appl. No.: 14/191,118

(22) Filed: Feb. 26, 2014

(65) Prior Publication Data

US 2015/0241552 A1  Aug. 27, 2015

(51) Int. Cl.
| | |
|---|---|
| *G01S 7/02* | (2006.01) |
| *G01S 13/02* | (2006.01) |
| *G01S 13/88* | (2006.01) |
| *G01S 13/89* | (2006.01) |
| *A61B 5/05* | (2006.01) |
| *H01Q 9/40* | (2006.01) |
| *H01Q 9/42* | (2006.01) |

(Continued)

(52) U.S. Cl.
CPC ............. *G01S 7/02* (2013.01); *A61B 5/0507* (2013.01); *A61B 5/4312* (2013.01); *A61B 5/7225* (2013.01); *G01S 7/026* (2013.01); *G01S 13/0209* (2013.01); *G01S 13/89* (2013.01); *H01Q 9/40* (2013.01); *H01Q 9/42* (2013.01); *H01Q 21/061* (2013.01); *A61B 2562/046* (2013.01); *G01S 13/88* (2013.01); *G01S 13/887* (2013.01)

(58) Field of Classification Search
CPC ..... G01S 7/024; G01S 7/026; G01S 13/0209; G01S 13/88; G01S 13/887; G01S 13/888; G01S 13/89; H01Q 21/061; A61B 5/05; A61B 5/0507; A61B 5/4312; A61B 5/7225; A61B 2562/046

USPC ..................................................... 342/22, 188
See application file for complete search history.

(56) References Cited

U.S. PATENT DOCUMENTS

| | | | |
|---|---|---|---|
| 4,630,051 A * | 12/1986 | Adams ................ | G01S 15/8979 342/133 |
| 4,717,916 A * | 1/1988 | Adams ................ | G01S 13/4454 342/107 |

(Continued)

OTHER PUBLICATIONS

Zhang, et al., "Multi-objective Experiment Using Ultrashort-Pulse Radar System for Breast Cancer Detection", Art, Science and Technology Center for Cooperative Research, Kyushu University, Japan, pp. 1-2.

(Continued)

*Primary Examiner* — Peter Bythrow
(74) *Attorney, Agent, or Firm* — Haynes and Boone, LLP

(57) ABSTRACT

Radar imaging for medical diagnosis addresses the need for non-ionizing and low-cost alternatives to conventional medical diagnosis methods, such as mammography x-ray techniques, which expose patients to ionizing radiation for cancer detection. An ultra wide band (UWB) sensor can produce very fine beams at the V- or W-bands using beam forming techniques developed specifically for wafer scale antenna arrays. The high bandwidth radio waves can penetrate tissue and resolve tissue anomalies with high-resolution. Pseudo-random coding creates a signal that allows the correlating receiver to extract very low energy reflected signals from background noise providing coding gain. An integrated panel of sensor antenna arrays enables rapid scanning of the subject area, such as breast tissue, to detect anomalies by eliminating the need for mechanical scanning (e.g., moving the sensors relative to the subject) because the wafer scale antenna array can instantaneously take the desired topographic picture of the subject area.

19 Claims, 14 Drawing Sheets

(51) Int. Cl.
*H01Q 21/06* (2006.01)
*A61B 5/00* (2006.01)

(56) References Cited

U.S. PATENT DOCUMENTS

| | | | | |
|---|---|---|---|---|
| 5,920,285 | A * | 7/1999 | Benjamin | G01S 13/89 342/22 |
| 6,396,450 | B1 * | 5/2002 | Gilbert | H01J 29/10 342/374 |
| 6,777,684 | B1 * | 8/2004 | Volkov | G01N 21/3581 250/341.1 |
| 6,967,612 | B1 * | 11/2005 | Gorman | G01S 7/412 342/175 |
| 7,081,850 | B2 * | 7/2006 | Small | G01S 7/282 342/134 |
| 7,791,556 | B2 * | 9/2010 | Mohamadi | H01P 1/184 343/795 |
| 7,830,989 | B2 * | 11/2010 | Mohamadi | G01S 7/032 343/850 |
| 7,839,283 | B2 | 11/2010 | Mohamadi | |
| 7,855,695 | B2 * | 12/2010 | Mohamadi | H01L 23/66 343/700 MS |
| 7,884,757 | B2 * | 2/2011 | Mohamadi | G01S 7/2926 342/118 |
| 7,884,776 | B2 * | 2/2011 | Mohamadi | H01L 23/66 343/850 |
| 8,077,072 | B2 | 12/2011 | Mohamadi et al. | |
| 8,154,339 | B2 * | 4/2012 | Zolghadri | H01P 5/12 330/124 R |
| 8,237,604 | B2 * | 8/2012 | Mohamadi | G01S 7/032 342/200 |
| 8,330,642 | B2 * | 12/2012 | Jin | G01S 13/9035 342/159 |
| 8,358,234 | B2 | 1/2013 | Mohamadi et al. | |
| 9,285,461 | B2 * | 3/2016 | Swirhun | G01S 7/026 |
| 2005/0270231 | A1 * | 12/2005 | Small | G01S 7/252 342/194 |
| 2009/0224964 | A1 * | 9/2009 | Raney | G01S 7/026 342/25 F |
| 2010/0060509 | A1 * | 3/2010 | Chambers | G01S 7/411 342/22 |
| 2010/0214150 | A1 * | 8/2010 | Lovberg | G01K 11/0066 342/22 |
| 2010/0225520 | A1 * | 9/2010 | Mohamadi | G01S 7/032 342/21 |
| 2011/0040176 | A1 * | 2/2011 | Razansky | A61B 5/0095 600/425 |
| 2011/0298680 | A1 * | 12/2011 | Shylo | A61B 5/015 343/762 |
| 2012/0001674 | A1 * | 1/2012 | Mohamadi | H01P 5/12 327/355 |
| 2012/0019406 | A1 * | 1/2012 | Sarkis | A61B 5/0507 342/22 |
| 2013/0307716 | A1 * | 11/2013 | Mohamadi | G01S 13/887 342/22 |
| 2014/0266866 | A1 * | 9/2014 | Swirhun | G01S 7/026 342/188 |

OTHER PUBLICATIONS

Chahat, et al., "New Method for Determining Dielectric Properties of Skin and Phantoms at Millimeter Waves Based on Heating Kinetics", IEEE Transactions on Microwave Theory and Techniques, vol. 60, No. 3, pp. 827-831, Mar. 2012.

Ocket, et al., "Dielectric Characterization of Biological Liquids and Tissues up to 110 GHz using an LTCC CPW Sensor", IEEE, BioWireleSS, pp. 43-45, 2013.

* cited by examiner

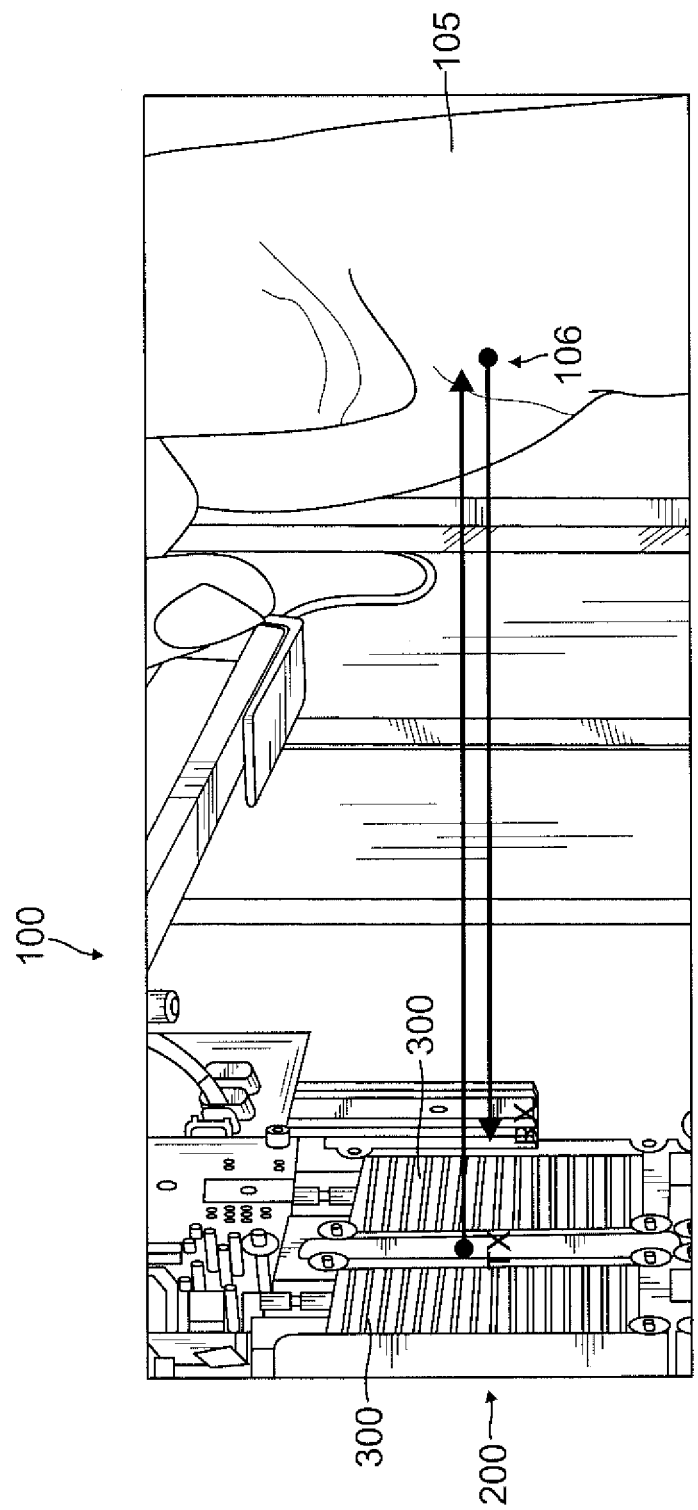

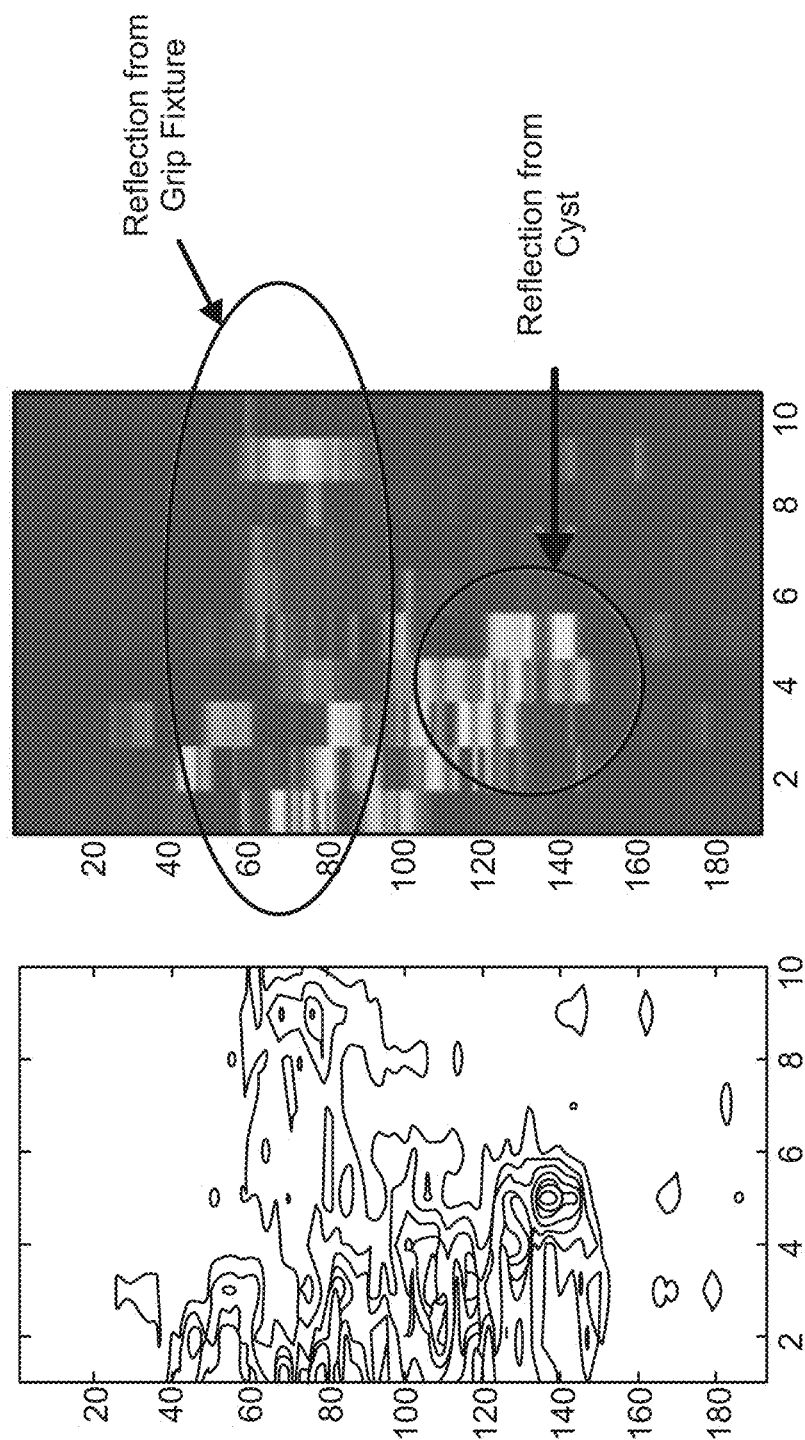

WAFER SCALE SENSOR ULTRA-WIDEBAND ARRAY FOR TISSUE DIAGNOSIS

BACKGROUND

1. Field of the Invention

The present invention relates generally to radar imaging systems and, more particularly, to ultra wideband radar systems integrated with wafer scale antenna arrays providing radar sensor and imaging for tissue diagnosis in the field of medicine.

2. Related Art

Among alternatives to conventional methods of breast cancer tumor detection such as mammography, microwave radar techniques appear to be one of the most promising as a result of their potential for being a non-ionizing and low-cost method. Recent research has shown that anomalous tissue may have dielectric constant different from normal living tissue so that differences in tissue relevant to medical diagnosis can be detected using microwave radar. Thus, techniques for microwave radar imaging of living organisms may have, in addition to cancer diagnosis, more general applicability for medical diagnosis.

BRIEF DESCRIPTION OF THE DRAWINGS

FIG. 1 is a perspective view of a wafer scale sensor system used for scanning a person's wrist in accordance with an embodiment of the present disclosure.

FIGS. 4A and 4B are display images produced by wafer scale sensor system showing a scan of a person's wrist such as seen in FIG. 1, in accordance with an embodiment.

Figure 2A:
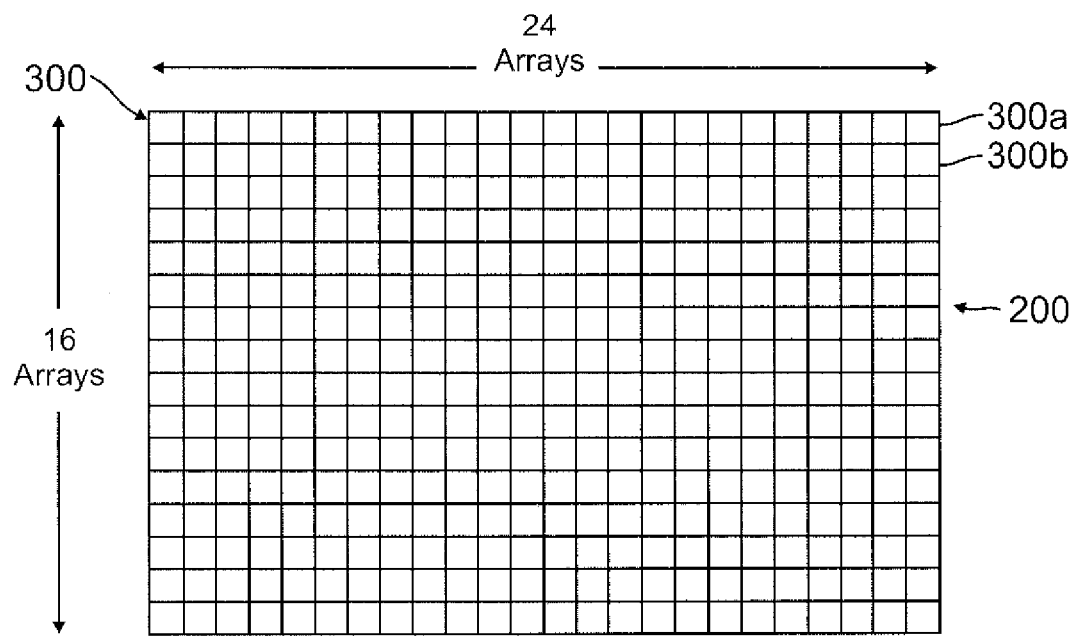
FIG. 2A is an elevation view diagram of a panel of antenna arrays for a wafer scale sensor system in accordance with one or more embodiments.

Embodiments of the present disclosure and their advantages are best understood by referring to the detailed description that follows. It should be appreciated that like reference numerals are used to identify like elements illustrated in one or more of the figures, in which the showings therein are for purposes of illustrating the embodiments and not for purposes of limiting them.

DETAILED DESCRIPTION

Methods and systems are disclosed for microwave radar imaging for medical diagnosis that address the need for non-ionizing and low-cost alternatives to conventional medical diagnosis methods. One or more embodiments, for example, may provide non-ionizing alternative to conventional mammography x-ray techniques, which expose patients to ionizing radiation, for breast cancer tumor detection. One or more embodiments, employ a version of an ultra wide band (UWB) sensor that can produce very fine beams at the V- or W-bands by using beam forming techniques developed specifically for wafer scale antenna arrays. Due to the high bandwidth (for UWB, in the range of about 1-10 GHz) of very short pulses at the V-band (e.g., about 40-75 GHz) and W-band (e.g., about 75-110 GHz), radio waves can penetrate tissue and resolve the tissue anomalies with high-resolution. For example, a millimeter-wave radio transmitter emits a train of very narrow pulses. The transiently radiated field impinges on tissues in its field of view and returns a reflected portion of that energy to a correlating receiver. Pseudo-random coding of the pulse train creates a signal and allows the correlating receiver to extract very low energy reflected signals from background noise (e.g., coding gain).

An innovative development uses a highly integrated array of sensor clusters (e.g., panel 200 of antenna arrays 300) for rapid scan of the subject area, such as breast tissue, to detect anomalies. The integrated array of sensor clusters can eliminate need for mechanical scanning (e.g., moving the sensors relative to the subject) because the wafer scale antenna based array can instantaneously take the desired topographic picture of the subject area, such as breast tissue, and present it in a high resolution display unit or transmit the image data and information wirelessly to a receiver unit. By way of contrast, in a typical synthetic aperture radar (SAR) imaging method, the radio moves along the target (or rotates around it) and scans the surface with a controlled beam width. However, a stationary and electronically steerable array antenna can scan the target with narrow beam width and at much higher speed. As an example a set of radio transceivers would suffice to achieve a precision detection and location (e.g., range and angle for two-dimensional (2-D)) capability. In order to construct and enhance a SAR type image, the solution of the Helmholtz differential equations for far field (generally distances>10×the wavelength) has been used. Generating a 3-D view of the target requires multiple transceiver arrays or multiple slices of 2-D images generated by application of electronic or mechanical surface scanning of the target. Multiple 2-D views can be captured by the antenna array and computationally merged using processing techniques like diffraction tomography.

Various embodiments may incorporate teachings from U.S. Patent Publication No. 2012/0001674 published Jan. 5, 2012, entitled "Wafer Scale Spatial Power Combiner", and U.S. Patent Publication No. 2013/0307716 published Nov. 21, 2013, entitled "Integrated Ultra Wideband, Wafer Scale, RHCP-LHCP Arrays", which are both incorporated by reference.

FIG. 1 is a perspective view of a wafer scale sensor system 100 used for scanning subject 105 of interest—in this example, a person's wrist—in accordance with an embodiment. FIG. 1 illustrates the position of the subject 105 wrist—having a cyst 106 of approximately 1 centimeter (cm) diameter—with respect to the panel 200 of antenna arrays 300. As indicated schematically in FIG. 1, panel 200 of antenna arrays 300 may transmit (TX) and receive (RX) radar signals using beam forming and power combining to produce, for example, narrow radio frequency (RF) pulses at a specific pulse repetition frequency (PRF) in the form of rapid wideband (narrow width) radar pulses at a chosen pulse repetition frequency (PRF) in the 1-10 GHz band. The pulses can penetrate different types of biological tissue with varying attenuation constant. The radar system 100 may, for example, transmit Gaussian pulses as short as a few pico-seconds wide with center frequency in the 1-10 GHz band, FIGS. 4A and 4B show examples of images that may be constructed by system 100 for the subject 105 wrist and cyst 106 at 60 GHz (e.g., V-band). Higher frequencies (e.g., 95 GHz, W-band) can produce even finer resolution images.

The electro-magnetic properties of materials, in particular the dielectric properties, e.g., relative permittivity ($\in_r$), exhibit a generally significant contrast in measured value between normal and malignant tissues. Permittivity, being dependent on the frequency of the electric field applied to the material, is usually expressed as a complex number. In general, the permittivity of tumors is much higher than normal tissue, hence, creates the capability to detect pronounced reflections with UWB RF interrogation such as that shown schematically in FIG. 1. In research and testing scenarios, measurements of relative permittivity of 10−j9 (conductivity of σ=0.4 S/m) for samples of human skin and relative permittivity of 50 (conductivity of σ=4.0 S/m) for malignant breast tissue have been reported. System 100 can exploit complex permittivity characterizations of healthy and malignant tissue for constructing diagnostic images of healthy and malignant tissue.

By measuring the path delay between transmitting and receiving antennas of panel 200 via any desired point in the tissue (e.g., subject 105), it is then possible to extract and time-align all the signals from that point. Repeated for all points in the tissue hundreds of times, the computational result yields an image in which the distinct dielectric properties of malignant tissue may then be presented. To minimize the clutter arising from the air-tissue interface, undesired reflections may be removed by cancelling out the systematic errors.

Simulation and imaging reconstruction of a single tumor, such as in breast tissue, can be modeled using system 100, performing simulations and measuring results of tests using malignant tissue detection with a panel 200 of arrays 300 of right-hand and left-hand circularly polarized (RHCP-LHCP) at 60 GHz ultra-wideband (UWB) antennas, using scanning impulses with picoseconds (ps) pulse width as a source, and measuring the reflected waves from the discontinuous layers of dielectric constant (permittivity differences). Since the transmitted pulse may be distorted due to the limiting bandwidth of antennas, it may be necessary to use wideband and non-dispersive antennas for the measurement.

FIG. 2A illustrates a panel 200 of antenna arrays 300 for a wafer scale sensor system 100 in accordance with one or more embodiments. In order to provide a cost effective, highly reliable, easily portable sensor system 100 with a small footprint, that is easy-to-operate, and is deployable in doctors' offices, health clinics, and hospitals, a highly compact scanning system 100 may be highly desirable, and thus may be implemented using wafer scale antenna arrays 300. FIG. 2A illustrates an embodiment of a panel 200 of 24×16 arrays 300 for the scanner of sensor system 100. In this arrangement 24 columns of TX-RX sensors with their antenna arrays 300 at the V- or W-band may be integrated. If, on one hand, the TX-RX sensors are implemented using one antenna array (not a separate pair of RHCP-LHCP array), then 16 rows of arrays 300 can be addressed for enhanced resolution. On the other hand, if the TX-RX sensors are implemented using pairs of TX-RX with polarization capability (e.g., a separate pair of RHCP-LHCP arrays 300a, 300b), then 8 rows of arrays 300 can be addressed. In the latter implementation, the advantage of RHCP-LHCP polarization may be an enhanced edge detection at the expense, however, of reduced resolution of image horizontally or vertically depending on orientation of panel 200.

Similar to the way in which RHCP-LHCP polarization may enhance edge detection of the tumor, use of a linear (e.g., 1×n) array for panel 200 may enhance resolution of the cross section of a tumor that has been detected and imaged. Furthermore, information from reflected signals analyzed by RHCP-LHCP polarization schemes may provide phase information that is also significant to identify the tissue classification, e.g., to detect anomalies.

Figures 2B, 2C:
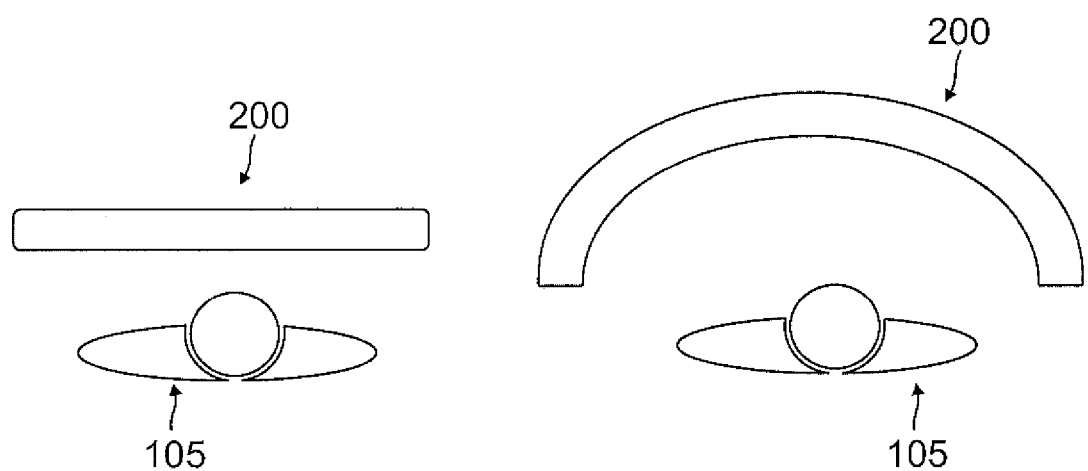
FIG. 2B is a plan view diagram of a panel of antenna arrays for a wafer scale sensor system in accordance with an embodiment.
FIG. 2C is another plan view diagram of a panel of antenna arrays for a wafer scale sensor system in accordance with an alternative embodiment.

Furthermore, panel 200 can be vertically flat or curved as shown, respectively, in FIG. 2B and FIG. 2C to address imaging relative to subject 105. The flat panel 200, as seen in FIG. 2B, may take less space and be easier to carry, while the radial panel 200, as seen in FIG. 2C, of sensor arrays 300 may reduce the load on imaging signal processing. Naturally, other arrangements of the array panel 200 can be pursued depending on the desired applications; for example, a double panel configuration of panel 200 may be used for internal body scanning.

Figure 3A:
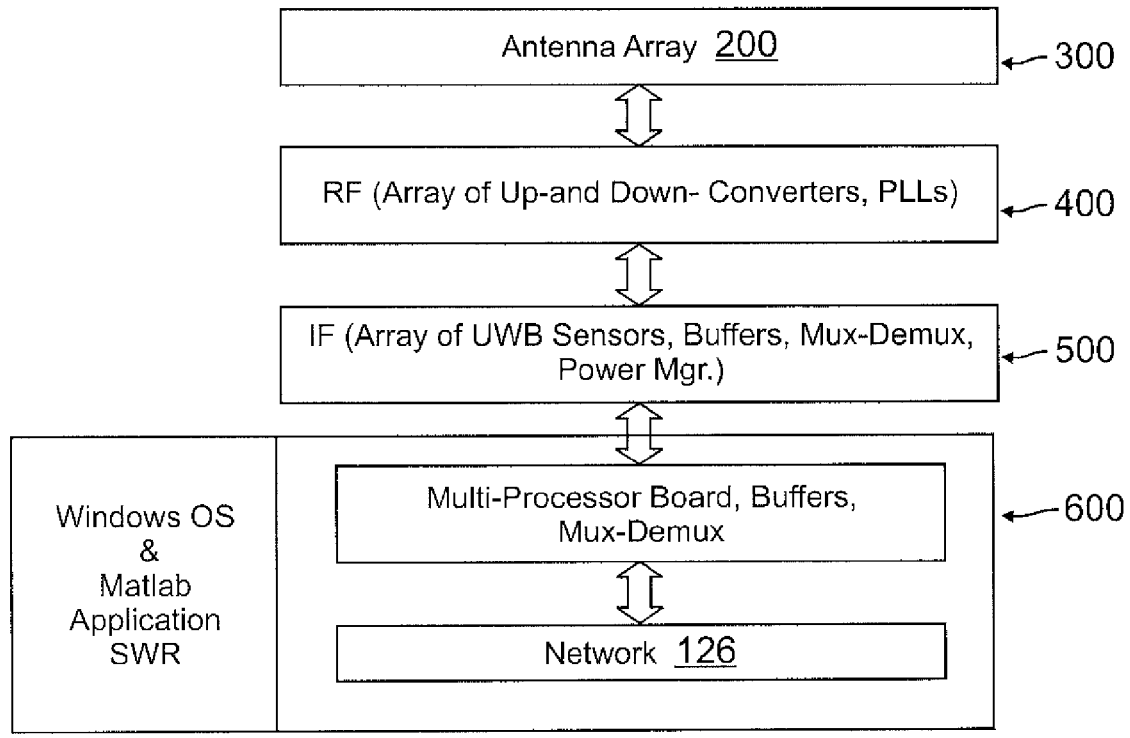
FIG. 3A is a top-level system block diagram for wafer scale sensor system.

FIG. 3A illustrates top-level distribution of system functionality, to address considerations relevant to hardware and software layers, for a wafer scale sensor system 100, in accordance with one or more embodiments.

Considerations at the level of panel 200 of wafer scale antenna arrays 300 may include: footprint of arrays 300 at V- or W-band and physical placement of the antenna arrays 300 and RF arrays 400 relative to each other; physical implementation using flip chip vs. using a single multi-layer board; physical placement of panel 200 on a scanner arm (not shown); and isolation of antenna elements 310 (see, e.g., FIG. 7) from the RF feeds (TX-RX) 302 (see, e.g., FIG. 7) with minimal insertion loss.

Considerations at the level of RF arrays 400 (e.g., up and down converters) may include: footprint of arrays 400 at V- or W-band and physical placement of the RF arrays 400 relative to panel 200; power distribution; phase lock loop (PLL) tuning; physical placement of RF arrays 400 on the scanner arm; and self calibration, RF diagnostics, and test flash.

Considerations at the level of intermediate frequency (IF) arrays 500 (e.g., 3-6 GHz UWB radar) may include: footprint of low power UWB array of signal processor chips (see, e.g., FIG. 3C); power distribution and power sharing with the RF arrays 400; PLL tuning hand-shake with the RF arrays 400; physical placement on the scanner arm; buffering, mux-demux of the Serial Peripheral Interface (SPI) or Universal Serial Bus (USB) based streamed data; upload and download capability of the registers, configuration files, and synchronization with the scanner arm; self calibration, diagnostic, and IF test flash for each channel; power distribution and power sharing with the IF array 500 and RF arrays 400; and physical placement on the scanner arm.

Considerations at the level of signal management board 600 (e.g., high-end processor board 130 shown in FIG. 3C) may include: buffering, mux-demux of the SPI or USB based streamed data; upload and download capability of the registers, configuration files, and synchronization with the scanner arm; interface with Windows OS (operating system) and Matlab® based parallel image processing (quad processor) and networking (e.g., network 126 also shown in FIG. 3C) capability to the operator as well as supervisory level locally and through the "cloud".

Figure 3B:
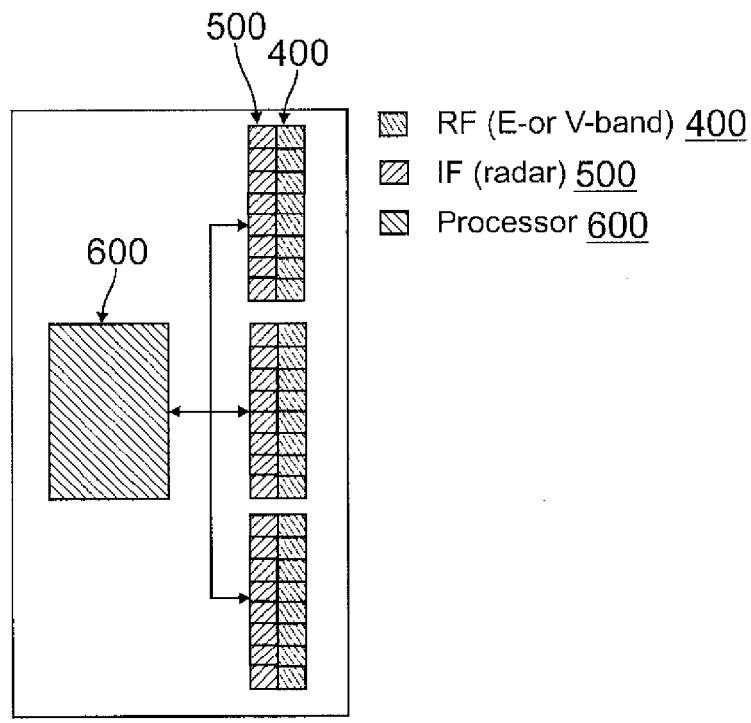
FIG. 3B is a system block diagram showing an example of an architecture for the diagram shown in FIG. 3A.

FIG. 3B is a system block diagram showing an example of a particular architecture for the diagram shown in FIG. 3A. FIG. 3B shows signal management board 600, IF arrays (e.g., 3-6 GHz UWB radar) 500, and RF arrays 400. Although not shown for clarity in FIG. 3B, each RF array 400 may be connected to a corresponding TX-RX transceiver 1000 and antenna array 300 as shown in FIG. 3C.

In one embodiment, for each of the three groups of eight arrays 500, 400 one of the transceivers may be used as a transmitter and all eight may be used as receivers. The transmitted pulse may be, for example, a first order Gaussian pulse with a center frequency of 4.35 GHz and a bandwidth greater than 2.5 GHz. The receivers may use a sampling on a continuous time binary value to achieve a sampling rate of 40 giga-samples per second (GS/s). Multiple number of the boards can be integrated to address the desired V-band or W-band multiple of 1×8 channels stacked for rapid millimeter wave scan of the tissue (subject 105) as shown in FIG. 3B.

In one embodiment using 8 radar chips, timing control may be implemented using field programmable gate array (FPGA) and SPI or USB concatenations for scanning and image construction. By proper processing of the phase shifting in the FPGA, beam steering function can be addressed as well. In such a sequence, as an example, a first transmitter only will trigger and all receiver channels will receive and then a second transmitter only will transmit, and so on. By proper phase management in the digital signal processor (DSP), the arrival time of the wave can be adjusted such that beam steering function is performed.

Figure 3C:
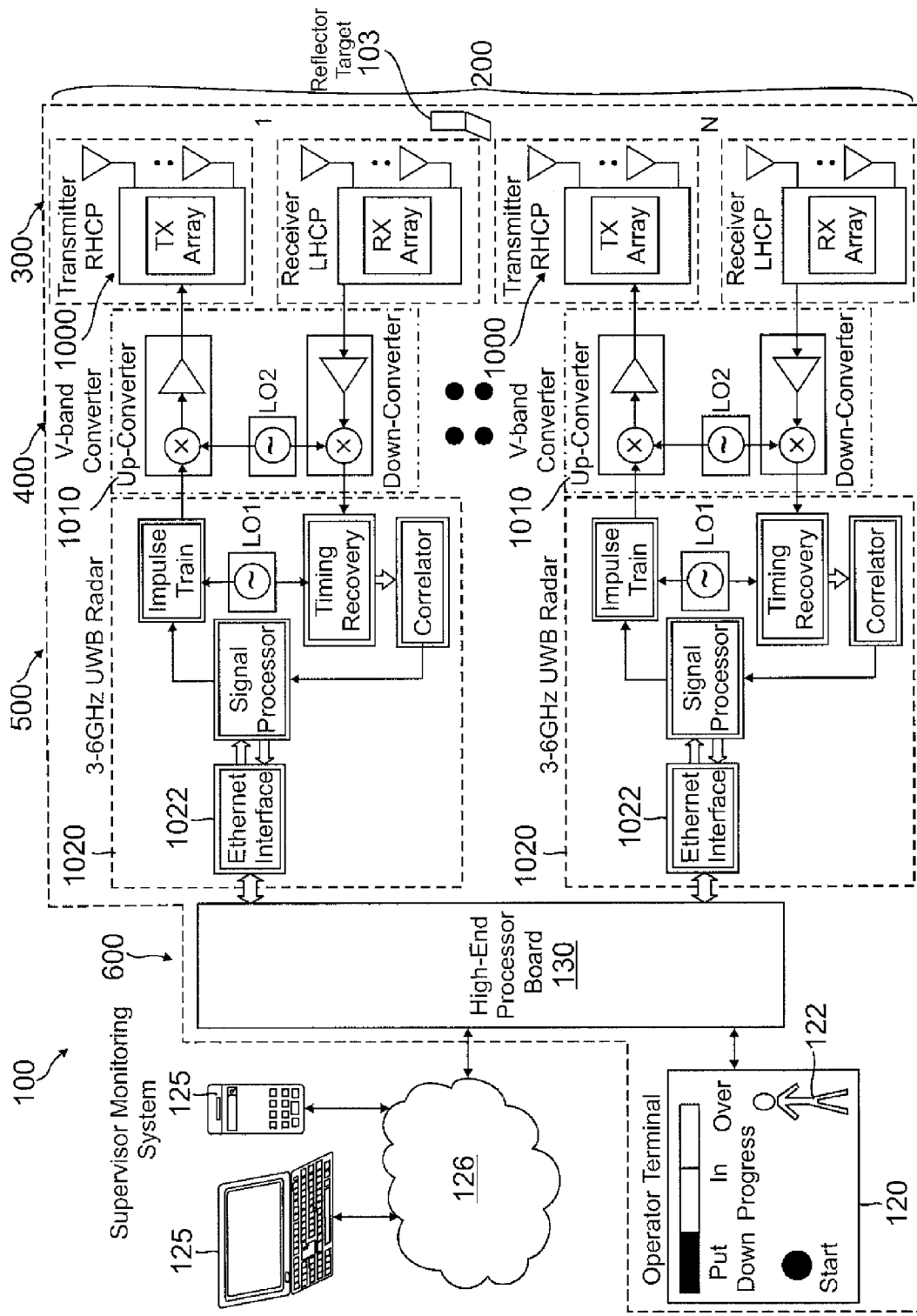
FIG. 3C is a circuit block diagram showing an example of an implementation for the diagram shown in FIG. 3A, in accordance with one or more embodiments.

FIG. 3C is a circuit block diagram showing an example of an implementation for the diagram shown in FIG. 3A, in accordance with one or more embodiments. Scanning system 100 may include a number, N, of radar transceivers, such as radar transceiver 1000 illustrated in FIG. 3C. N may be any number. For example, N may be 24×6=384 radar transceivers 1000 for the embodiment described in FIG. 2A, or N may be 24 for the embodiment described in FIG. 3B. System 100 may use an array of transceivers 1000 in which each transceiver is a single-chip radar transceiver realized in complementary metal oxide semiconductor (CMOS) process that may reduce the cost, weight, and energy consumption of system 100 compared to multi-chip radar transceiver implementations, may provide a set of completely isolated transceivers 1000 for system 100, may provide modularity of the system, and may facilitate extension of its application to medical diagnostic scanning.

In one or more embodiments, the system 100 may employ a either a linear (e.g., 1×n) or rectangular array (e.g., m×n, panel 200) including one or more sets of multiple single-chip radar transceivers mounted on single FR4 substrate printed circuit boards. In one embodiment, a multiple number of the single-chip radar transceiver boards may be integrated to implement an N-channel linear array for rapid millimeter-wave scan of the subject 105. One of the transceivers may be used as a transmitter and all of the multiple (for each board) or N transceivers may be used as receivers. The transmitted pulse may be, for example, a first order Gaussian pulse with a center frequency of 4.35 GHz and a bandwidth greater than 2.5 GHz. The receivers may use a sampling on a continuous time binary value to achieve a sampling rate of 40 giga-samples per second (GS/s).

Each transceiver 1000 may be connected via an Ethernet interface 1022 with a processor 130 that may, for example, perform processing that combines data from all transceivers 1000—whether in a rectangular array or a linear array that is moved to scan the scanning area defined by panel 200—to provide an image, such as image 122, on a display 120. System 100 may also include a supervisor monitoring system 125 that may communicate with processor 130 via a network 126, as shown, which may include a private secure network, for example, or the Internet.

In system 100, an array of independent transceivers 1000 (using UWB radar of primary processing unit 1020 as intermediate frequency (IF) and up- and down-converters of RF module 1010 in RF) may be used for extreme near-field imaging. In FIG. 3C, an arrangement with an integrated IF (radar) board for each transceiver 1000 may operate at 1-10 GHz bandwidth. Results from a mathematical model of system 100 incorporating the inter-sample delay variations show that process variations are a strong influence on image degradation and a factor that is not easily rectified. In one or more embodiments, the problem of inter-sample delay variations may be addressed by direct calibration of the system 100 using one or more reflectors 103 (also referred to as a calibration target) positioned at known locations in the image.

FIGS. 4A and 4B are display images produced by wafer scale sensor system 100 showing a scan of a person's wrist such as seen in FIG. 1, in accordance with an embodiment. As seen in FIG. 1, subject 105 (person' wrist) may be scanned at a range of a few inches from panel 200 comprising antenna arrays 300. FIG. 4A shows constant power contours for the scan of subject 105 and FIG. 4B shows a spatial image of the hand tissue and anomaly tissue (e.g., cyst 106). The image of the hand shown in FIGS. 4A and 4B may be constructed using a 20×20 position (e.g., panel 200 with TX-RX sensors implemented using pairs of TX-RX with polarization capability, e.g., a separate pair of RHCP-LHCP arrays 300a, 300b arranged as 20 rows by 10 columns of array 300 pairs) emulated wafer scale antenna array arrangement taken in one second of exposure, where further signal processing of the image demonstrates existence of major change in relative permittivity, showing the anomalous tissue (e.g., cyst 106) in contrast to normal tissue (e.g., remainder of person's hand). The transmitted power from IF 500 (e.g., 3-6 GHz UWB radar) was about −13 dBm, the RF 400 (e.g., up and down converters 1010) transmitted power was less than 50 mW and the beam widths of the TX-RX antennas (e.g., transceivers 1000 and wafer scale antenna arrays 300) were about 4 degrees. RF operating frequency was from 57 to 60 GHz.

Figure 5B:
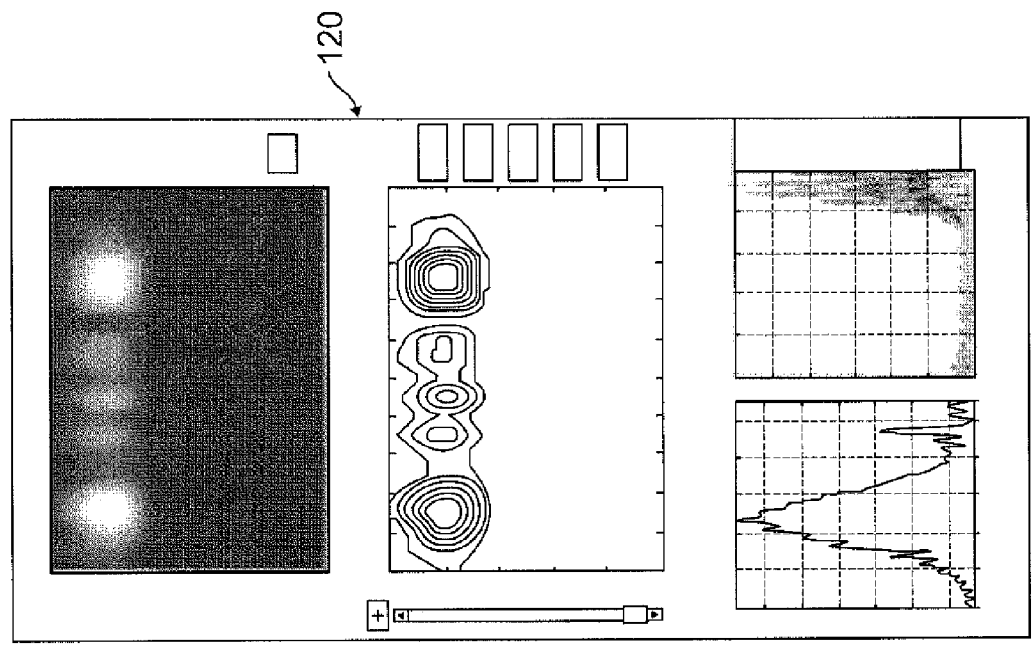
FIG. 5B is an example of an image reconstruction display for the scenario shown in FIG. 5A, in accordance with an embodiment.
Figure 5A:
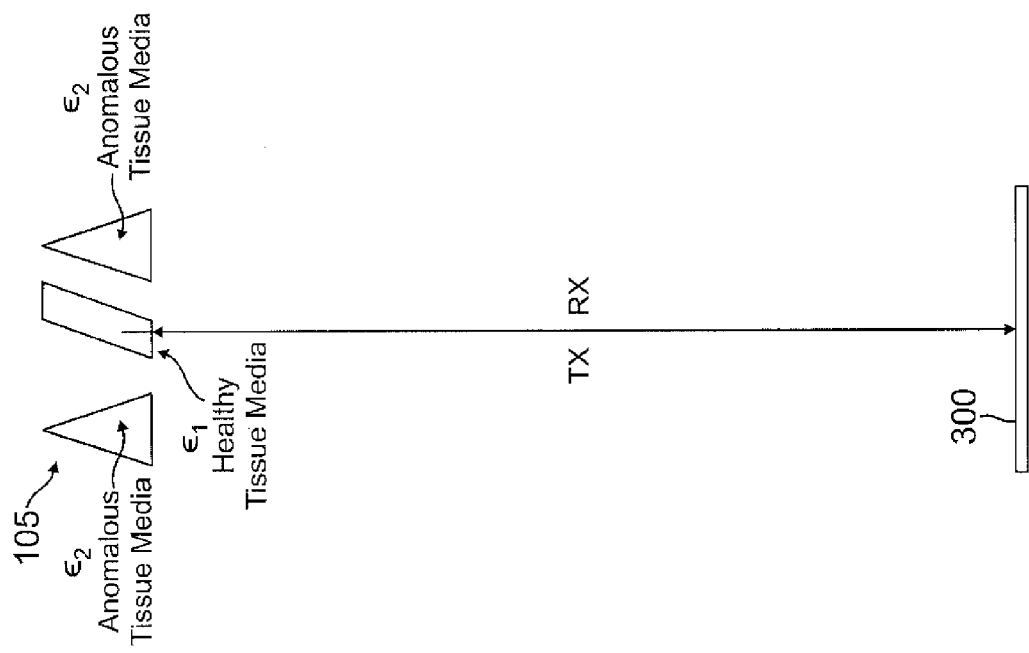
FIG. 5A is a diagram of physical test scenario for scanning body tissue.

FIG. 5A is a diagram of physical test scenario for scanning body tissue; and FIG. 5B shows a graphical user interface display 120 for wafer scale sensor system 100 with an example of an image reconstruction display for the scenario shown in FIG. 5A. A series of different shape material with high relative permittivity ($\in_2$) inside a low permittivity ($\in_1$) media were subjected to RF scanning and then the reflection image was constructed using a finite difference time domain (FDTD) simulation tool. A method of correlation of the reflected signal with the known transmitted pulse has the lowest detection error and is selected in the simulations. The antenna may be moved along the x-axis to scan the objects. A snapshot of the simulated scenario with the constructed image of multiple objects has been depicted in FIG. 5B. A Gaussian pulse of 20 GHz bandwidth centered at 60 GHz may be simulated to interrogate the objects located at 49 cm of the antenna plane. Scan is achieved by 21 scan points 2.5 cm apart. FIG. 5B illustrates the constructed image of the subject 105 with highly reflective material in air. As described above, a relative permittivity of 10−j9 (conductivity of σ=0.4 S/m) for human wrist skin and relative permittivity of 50 (conductivity of σ=4 S/m) may be typical.

Figure 6A:
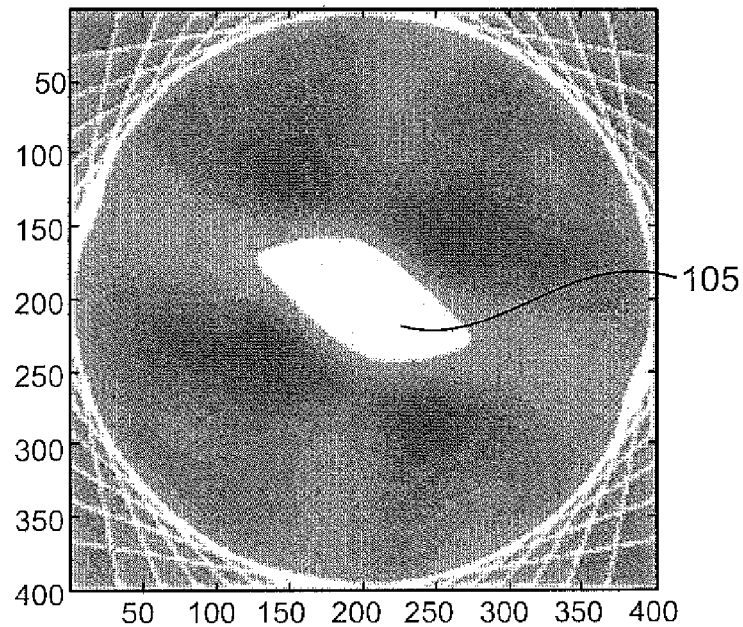
FIGS. 6A and 6B are examples of image construction displays for various test subjects, in accordance with one or more embodiments.
Figure 6B:
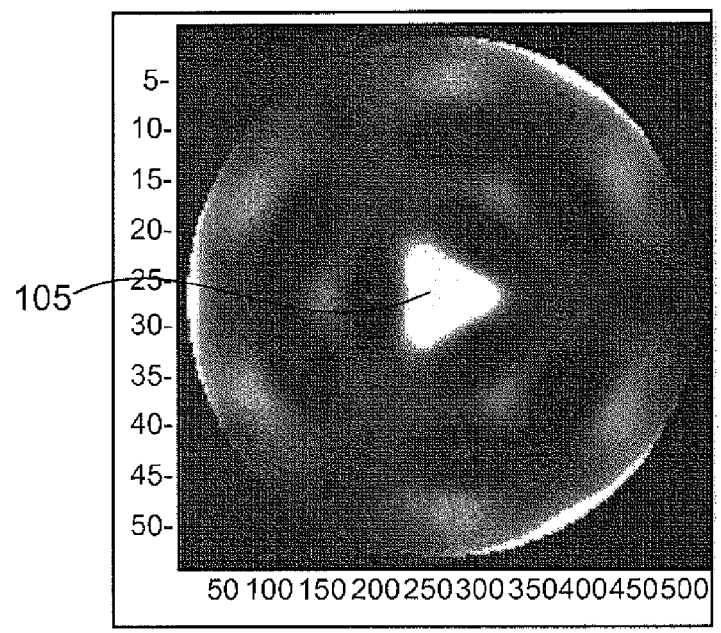

FIGS. 6A and 6B are examples of image construction displays for test subjects 105; FIG. 6A shows image construction from a Circular Scan of Parallelogram shaped test subject 105; and FIG. 6B shows image construction from a Circular Scan of a Pyramid shaped test subject 105. In this scenario, the radar antenna (e.g., array 300) circles around and scans the target (e.g., subject 105) from different angles. This mode of operation gives a 2-D view of the object (e.g., subject 105). In a more practical scenario, a number of antennas (typically 8-16) may be installed in the radar front-end to interrogate different angles. FIG. 6A shows the scanned image resulting from circular scanning a parallelogram with 36 scan points at 10° steps. FIG. 6B shows the scanned image result of circular scanning a highly reflective pyramid.

Figure 7:
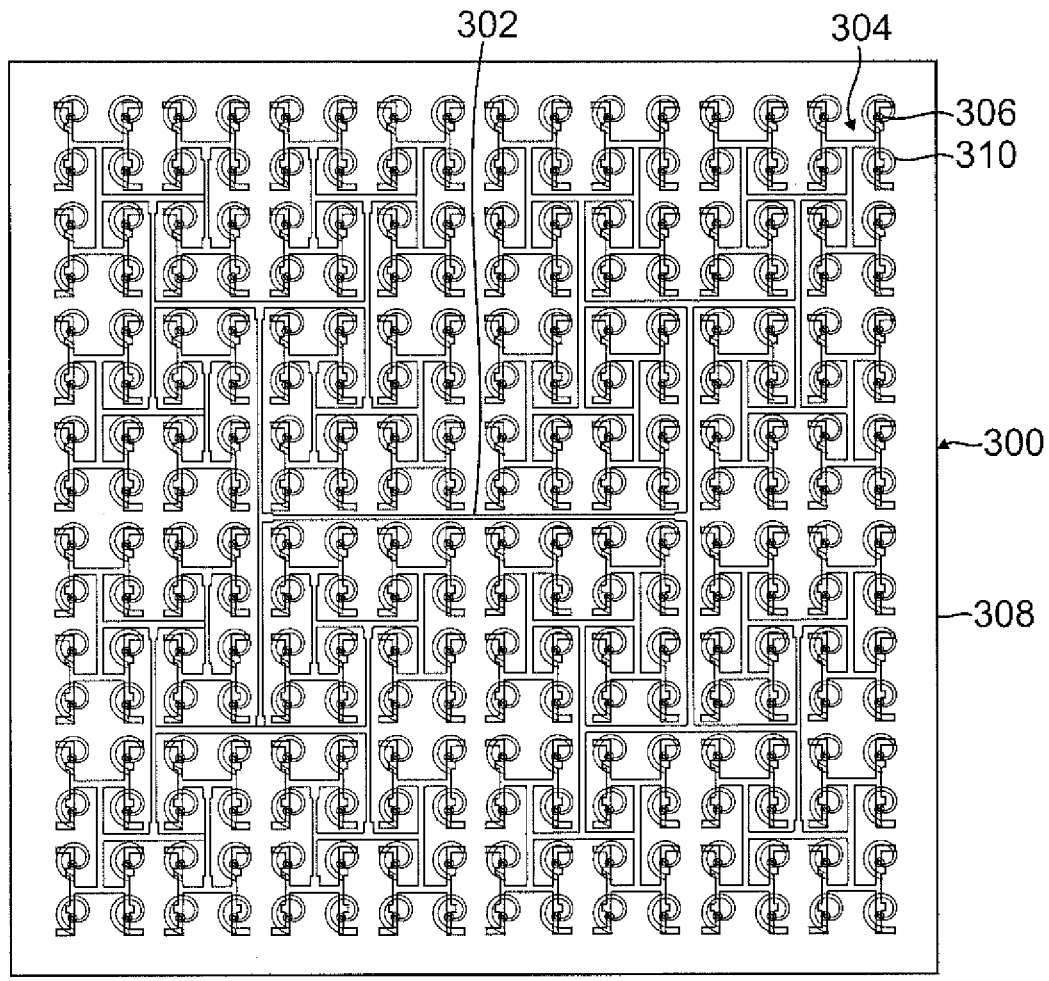
FIG. 7 is a plan view diagram showing antenna element and feed network layout for a wafer scale antenna array, in accordance with an embodiment.

FIG. 7 is an illustration of a wafer scale antenna array 300 showing antenna element and feed network layout for a 16-by-16 antenna element array 300, in accordance with an embodiment. Wafer scale antenna array 300 may be used, for example, to identify the phase of an object, in case that the array is used as part of a radar transmitter and receiver. In a fully integrated wafer-scale system, the array may be fed from the center as seen in FIG. 7 showing a central array feed 302. Wafer scale antenna array 300 may include an H-tree feed network 304, vias 306, ground plane shield 308, and UWB spiral antenna plates 310 as a 16-by-16 wafer-scale LHCP array.

Figure 8:
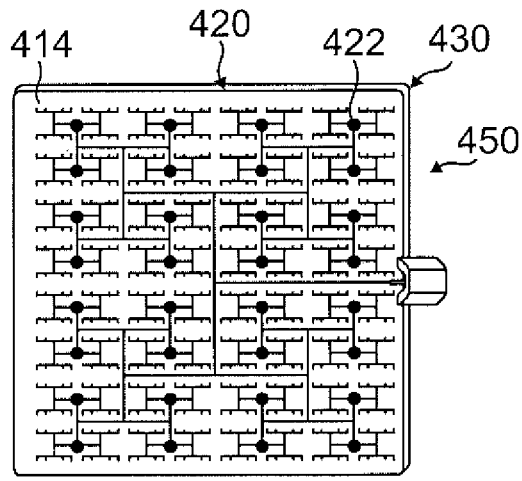
FIG. 8 is a schematic diagram showing an example of power or low noise amplifier placement for an antenna array, in accordance with an embodiment.
Figure 9A:
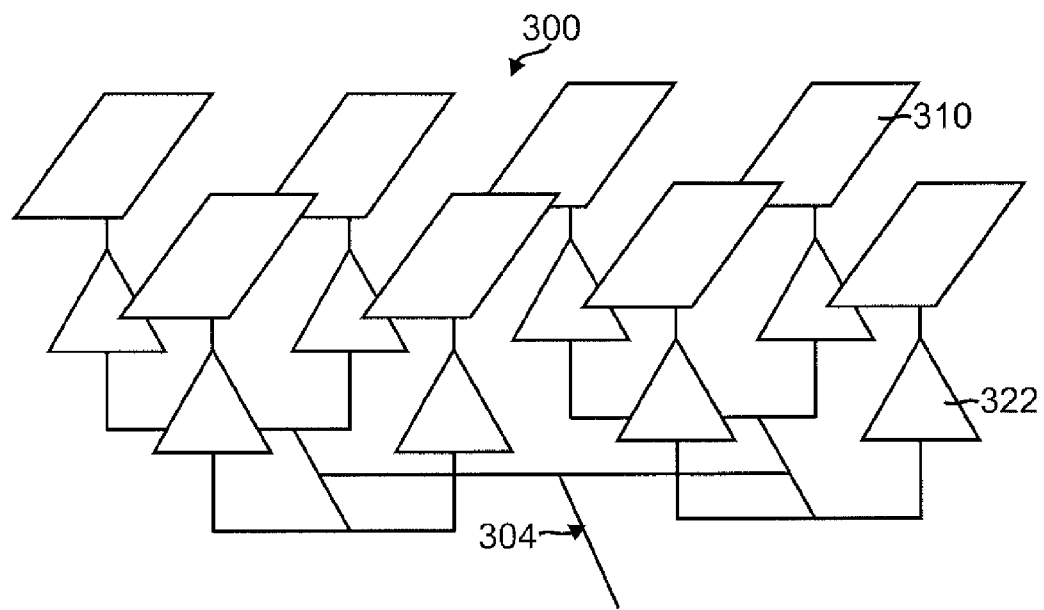
FIGS. 9A and 9B are schematic diagrams showing different examples of power amplifier placement in a feed network for an antenna array, in accordance with an embodiment.
Figure 9B:
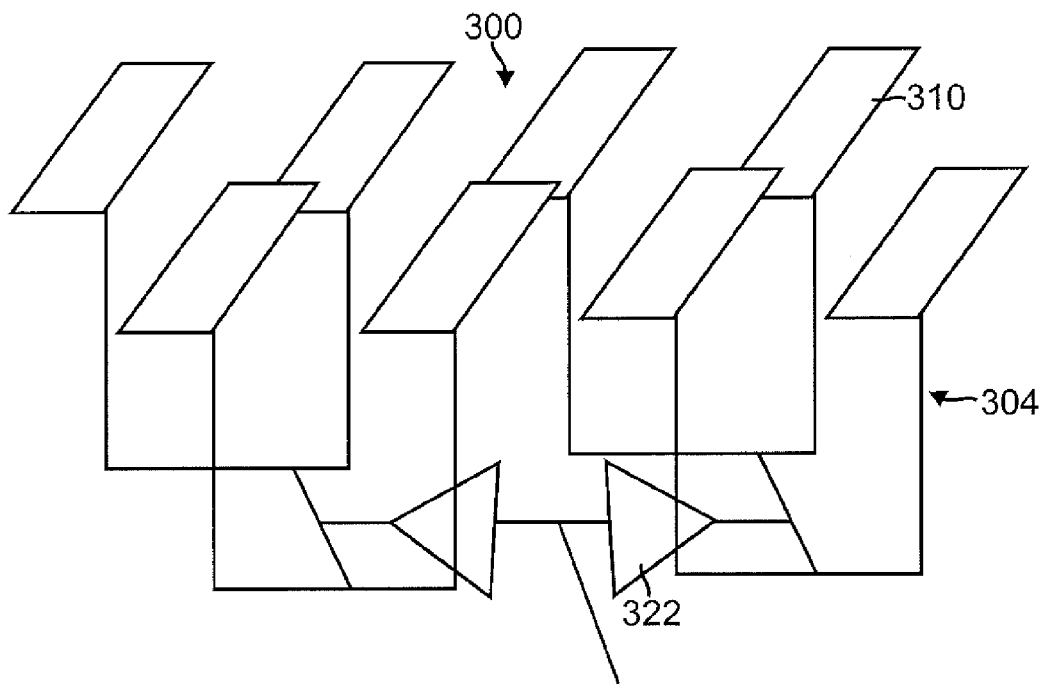

FIG. 8 shows an example of power amplifier or low noise amplifier placement for an antenna array, such as arrays 300, 300a, or 300b. FIG. 8 shows a 16-by-16 antenna array 420, with 16 power amplifiers 422—which may be implemented in Gallium-Nitride (GaN), for example—feeding 256 antenna elements 414. In a similar example, the 16-by-16 antenna array 420 may be implemented in Gallium-Arsenide (GaAs) with 64 power amplifiers 422 (placed differently as illustrated by the example of FIGS. 9A and 9B) feeding the 256 antenna elements 414. Array 420 may be referred to as a "tile". The spatial combiner of each tile may be manufactured using an H-tree technique of the planar active array, as seen in FIGS. 7 and 8. Planar antenna array 420 may be disposed "on top of" another similar array 430 having either the same or orthogonal polarization so that arrays 420 and 430 are layered. Thus, a wafer scale antenna module 450 may include integration of the wafer scale RHCP layer antenna array 430 with another layer of LHCP array 420 on top (or bottom). In one or more embodiments, integrated RHCP and LHCP layers 420, 430 may operate as a wafer scale antenna module 450 that can transmit through the LHCP array and receive waves in the LHCP array as well as the RHCP array, and, conversely, the integrated RHCP and LHCP layers may perform as a wafer scale antenna module 450 that can transmit through the RHCP array and receive waves in the LHCP array as well as the RHCP array.

FIGS. 9A and 9B show an example of power amplifier placement variation for a feed network for an antenna array 300, which may provide flexibility to adjust for differing power and thermal requirements of various materials (e.g., Si, SiGe, GaN, GaAs, and InP) used to implement array 300. For example, optimal dispersion of power amplifiers 322 in feed network 304 for feeding antenna elements (e.g., spiral antenna plates 310) may differ from providing one power (or low noise in the case of a receiving antenna array) amplifier 322 per antenna element, as shown in FIG. 9A, to providing one power (or low noise in the case of a receiving antenna array) amplifier 322 per several antenna elements, for example, four, as shown in FIG. 9B.

Figure 10B:
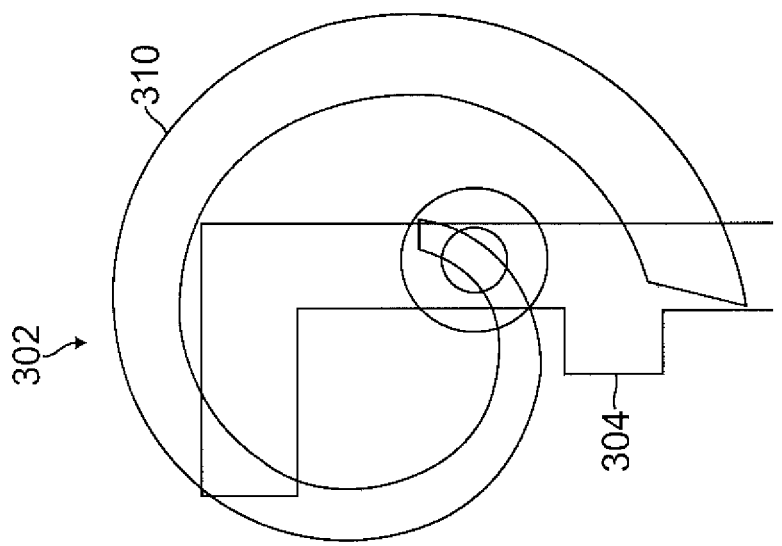
FIGS. 10A and 10B are plan view diagrams illustrating unit cells of an antenna array for left hand circularly polarized (LHCP) and right hand circularly polarized (RHCP) performance, in accordance with an embodiment.
Figure 10A:
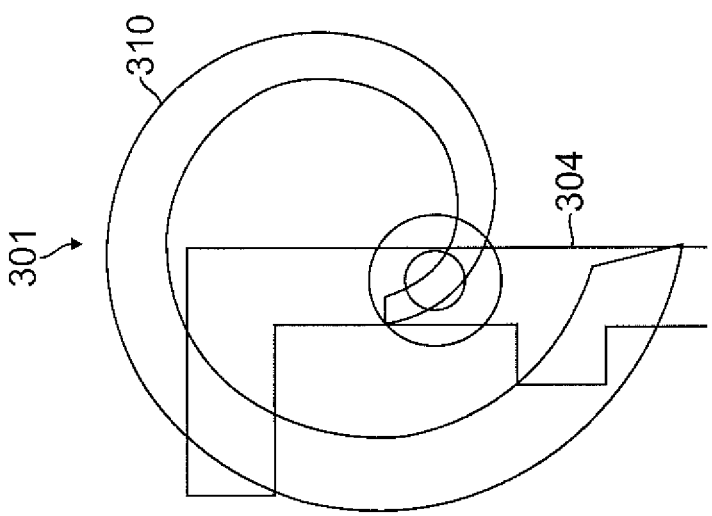

FIGS. 10A and 10B illustrate unit cells 301, 302 of an antenna array (e.g., wafer scale antenna array 300) for left hand circularly polarized (LHCP) and right hand circularly polarized (RHCP) performance. The form and dimensions of each spiral plate 310 may be defined or determined using the following equations.

Outer spiral circumference may be defined by Equations (1) and (2):

$$Xo=Ao*d*\mathrm{Cos}(Bo+ba)+\mathrm{off}+Cox \qquad (1)$$

$$Yo=Ao*d*\mathrm{Sin}(Bo+ba)+\mathrm{off}+Coy \qquad (2)$$

For 95 GHz operation, for example, the following values may be used:

Ao=5 to 101
Bo=0.08 to 1.76
ba=6.2
d=4.5
off=0
Cox=109
Coy=189

Inner spiral circumference may be defined by Equations (3) and (4):

$$Xi=Ai*d1*\mathrm{Cos}(Bi+ba)+\mathrm{off}+Cix \qquad (3)$$

$$Yi=Ai*d1*\mathrm{Sin}(Bi+ba)+\mathrm{off}+Ciy \qquad (4)$$

For 95 GHz operation, for example, the following values may be used:

Ai=5 to 101
Bi=0.08 to 1.76
ba=6.2
d1=6.0
off=0
Cix=109
Ciy=189

Figure 11:
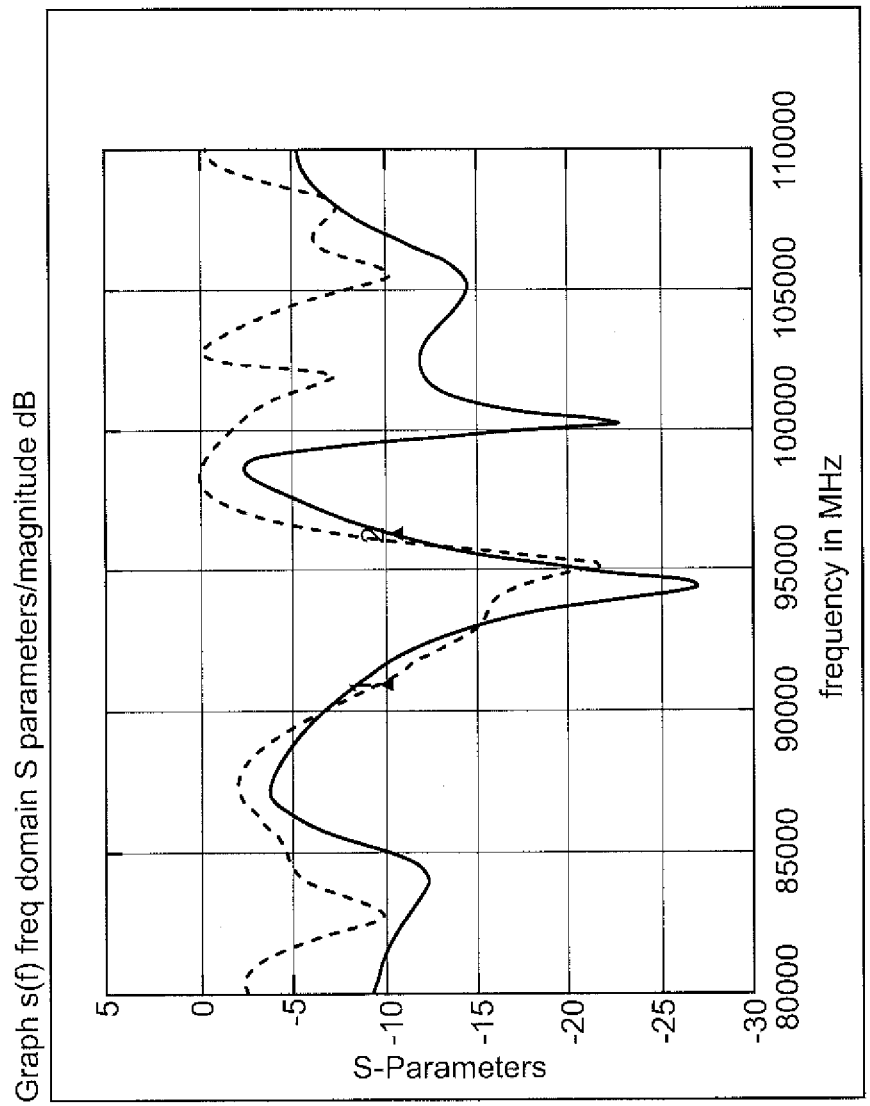
FIG. 11 is a graph illustrating insertion loss vs. frequency for a 16-by-16 LHCP antenna array, such as that shown in FIG. 7, in accordance with an embodiment.

FIG. 11 is a graph illustrating insertion loss vs. frequency for a 16-by-16 LHCP antenna array, such as that shown in FIG. 7, in accordance with an embodiment. FIG. 11 shows a graph of insertion loss (in dB) vs. frequency (in MHz) using S-parameters (e.g., a mathematical construct that quantifies how RF energy propagates through a multi-port network; for example, S11 may refer to the ratio of signal that reflects from port one for a signal incident on port one) for a 16×16 LHCP antenna array (e.g., wafer scale antenna array 300) which operates around a center frequency of 95 GHz.

Figure 12A:
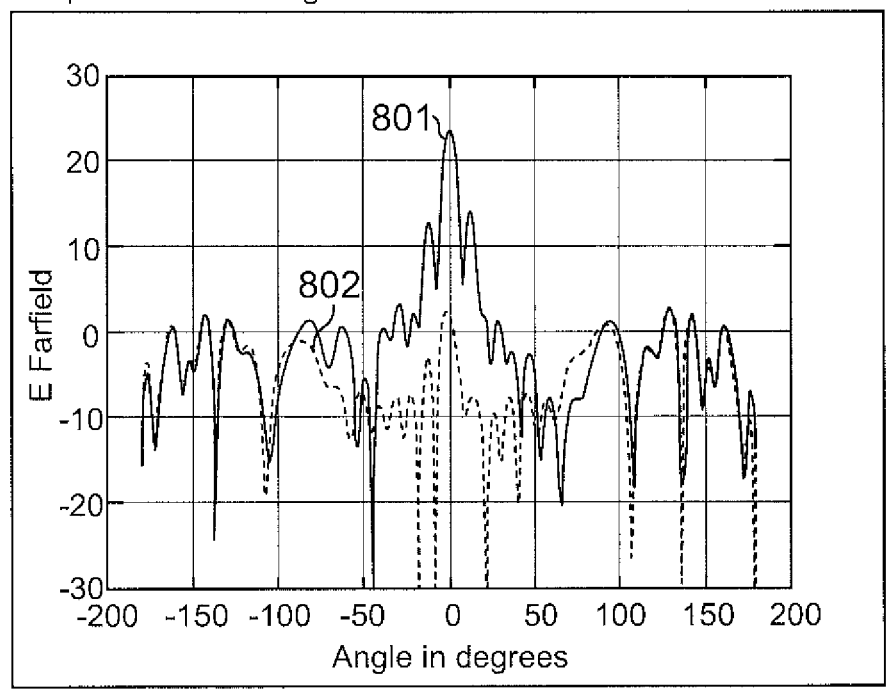
FIGS. 12A and 12B are graphs showing co-polarization and cross polarization for wafer scale, LHCP and RHCP antenna arrays, in accordance with an embodiment.
Figure 12B:
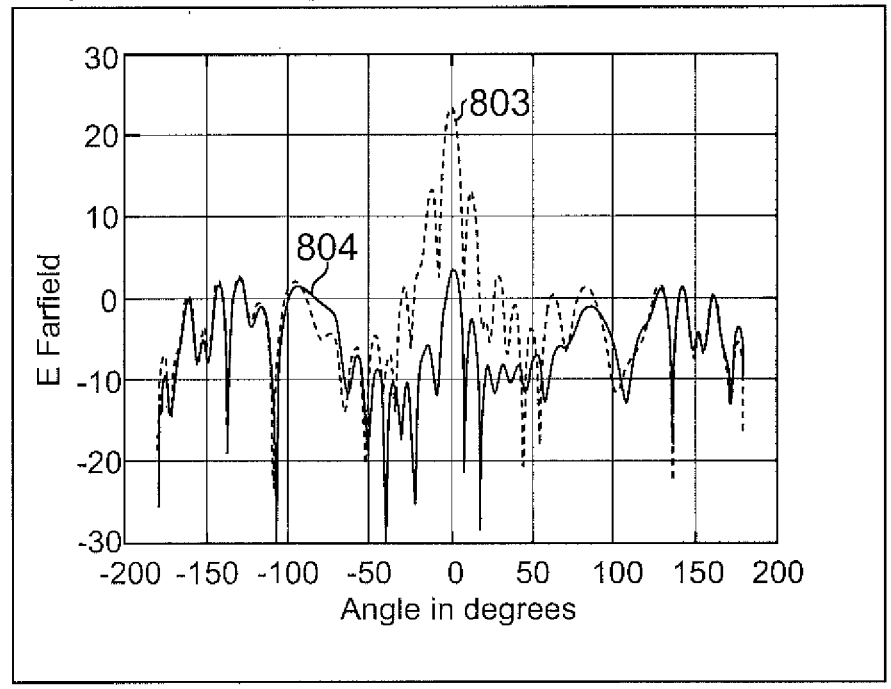

FIGS. 12A and 12B show co-polarization and cross polarization graphs for wafer scale, LHCP and RHCP antenna arrays (e.g., similar to wafer scale antenna array 300). FIG. 12A shows wafer scale beam forming of an LHCP array with left-hand circular polarization (co-polarization) beam 801 and cross polarization 802. As can be seen from the graph, beam width of better than 4 degrees can be obtained, with a 22 dB gain difference for cross polarization suppression of the RHCP wave 802. FIG. 12B shows similar results for wafer scale beam forming of an RHCP array (e.g., similar to wafer scale antenna array 300) with right-hand circular polarization (co-polarization) beam 803 and cross polarization (LHCP) 804.

Figure 13:
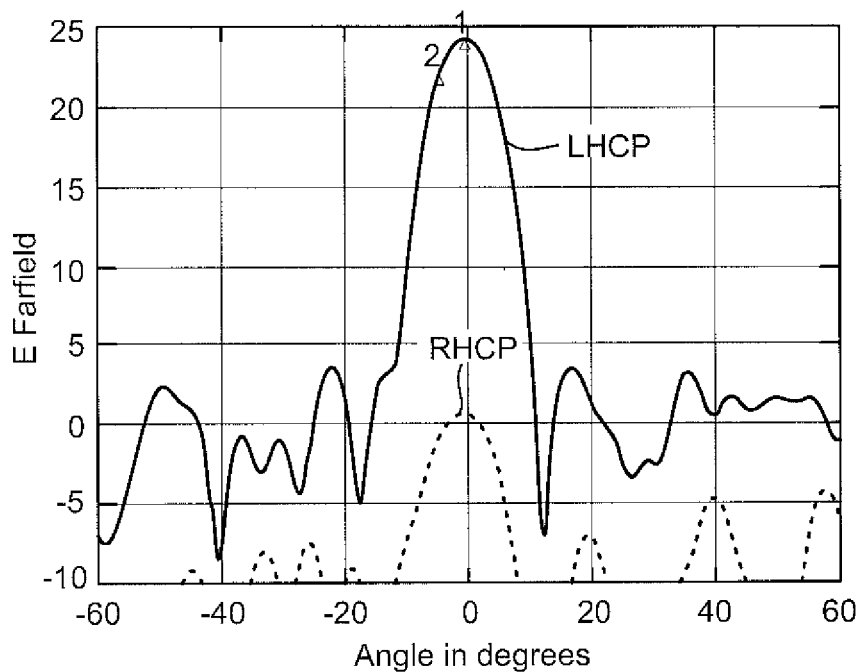
FIG. 13 is a graph showing an example of polarization and enhancement of side lobe suppression for a four-by-four element collimated antenna array, in accordance with an embodiment.

FIG. 13 shows a graph of an example of polarization and enhancement of side lobe suppression for a 4×4 element collimated antenna array. In one embodiment, an "out-of-phase squeezing" of the transmitted waves permits a smaller array to deliver similar gain, beam width, and polarization properties with substantially reduced number of array elements compared to a larger array such as the (256-element) antenna array 300 and may reduce the need for integration of complex power amplifiers with the antenna array, reducing the integration level, power consumption, and cost. In one embodiment, the enhancement using "out-of-phase squeezing" may permit using a 4-by-4 element (16 antenna elements) or 8×8 elements (64 antenna element) array instead of, for example, the implementation of the 16×16 (256 antenna elements) antenna array 300 such as shown in FIG. 7. Such an antenna size reduction confers the capability to reduce various radar system sizes by a factor of 4 as well as packing alternating right-hand circularly polarized (RHCP) and left-hand circularly polarized (LHCP) 4×4 arrays in a planar surface to provide higher radar image resolution and phase contrast with minimal thickness of the arrays.

In addition, use of a separate wafer scale collimator layer 1100 (see FIG. 14B) that is separated from the antenna array by a certain distance may be implemented. Such a collimator may be implemented as a 4×4 array of Teflon based (e.g., $\in_r=2.0$, where $\in_r$ is the relative permittivity of the material as opposed to the vacuum permittivity $\in_0$) collimators that produce a beam width of approximately 8.0 degrees and a gain of 24.4 dB with 24 dB cross polarization. The index of refraction (or permittivity) of the collimators can vary among various embodiments.

Figure 14A:
FIG. 14A is a diagram showing a cross section of a collimator for an antenna array, in accordance with an embodiment.
Figure 14B:
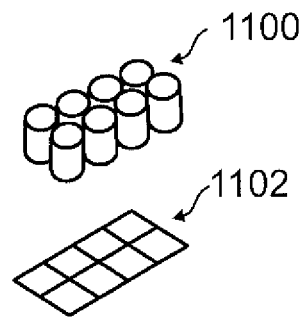
FIG. 14B is a perspective diagram of a collimator and a pair of four-by-four element collimated antenna arrays, in accordance with an embodiment.

The graph in FIG. 13 shows co-polarization and cross-polarization of the LHCP radiation and RHCP radiation of the 4×4 array 1102 with Teflon wafer-scale collimator 1100 shown in FIG. 14B. The size of the 4×4 array 1102 operating at 95 GHz may be about 5.6 mm by 5.6 mm. FIG. 13 shows side lobes are below 3 dB with a better than 20 dB side lobe suppression compared to the 16×16 array 300 that has two strong side lobes at 12 dB. Suppression of side lobes may be a critical factor for clear radar imaging with high contrast and high antenna efficiency (e.g., greater than 95%).

FIG. 14A is a diagram showing a cross section of a collimator for an antenna array such as shown in FIG. 14B; and FIG. 14B is a perspective diagram of a collimator layer and a pair of 4-by-4 element collimated antenna arrays, in accordance with an embodiment. FIG. 14B depicts the implemented collimator 1100 at the position, relative to array 1102, of enhancing the gain and reducing side lobes. As shown in FIG. 10B, one 2×2 LHCP array and one 2×2 RHCP array may be integrated in the same substrate side by side. Spacing between the collimator 1100 and the array plates 1102 may be about 20 mm for a combination of collimator patterns with each protrusion upward and inward with effective radius of 20 mm and total thickness of 5 mm. Four double-sided protrusions may be placed atop of each 2×2 sub-array.

Figure 15A:
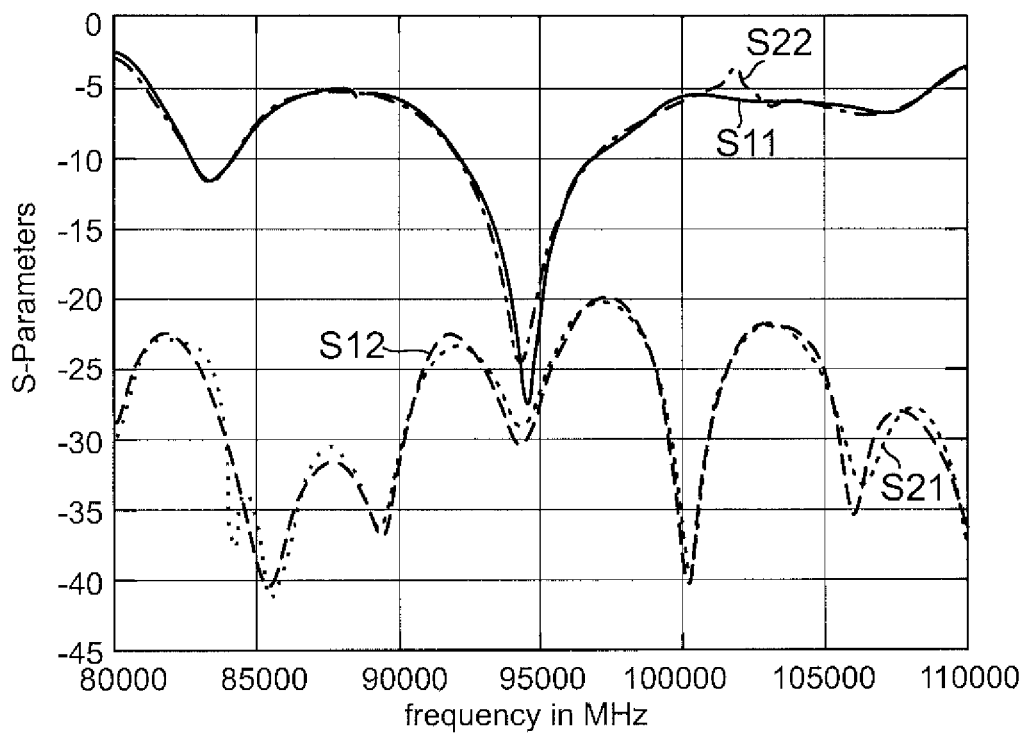
FIGS. 15A and 15B are graphs illustrating an example of cross-coupling and cross-polarization for a pair of four-by-four element antenna arrays, in accordance with an embodiment.
Figure 15B:
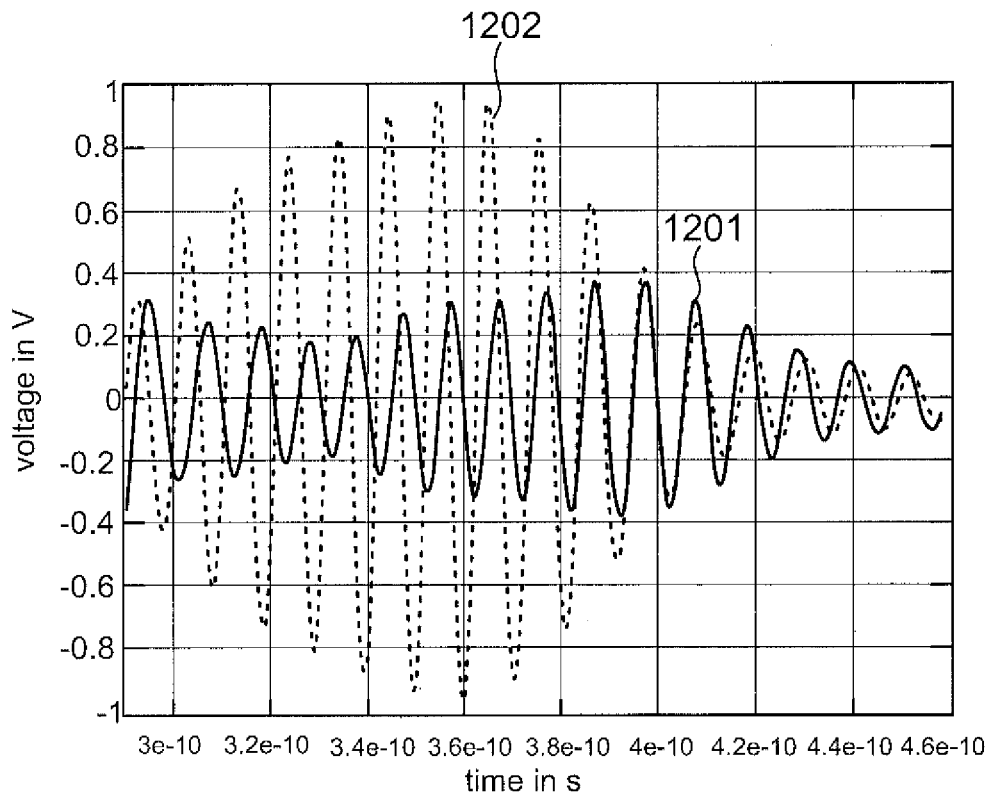

FIGS. 15A and 15B are graphs illustrating an example of cross-coupling and cross-polarization for a pair of four-by-four element antenna arrays, in accordance with an embodiment. To verify lack of cross coupling, the S11, S12, S22, and S21 S-parameters, as shown in FIG. 15A, were measured.

FIG. 15B shows a graph of voltage 1201 cross coupled during transmission and then returned, in response to a modulated UWB Gaussian pulse 1202, from a metallic reflector placed 53 mm away from the (co-polarized) array 1102 for simulation purposes, illustrating that the returned voltage 1201 from the metallic reflector is highly detected by the cross-polarized array 1102.

Such simulation results, summarized in Table 1, may show, for example, that a 4×4 element array may have nearly the same gain, superior side lobe suppression, and enhanced cross polarization suppression, while its size is about 25% of an 8×8 array and 6% of a 16×16 array.

TABLE 1

| | System | |
| --- | --- | --- |
| | 16 × 16 | 4 × 4 with Collimator |
| Center Frequency (GHz) | 95 | 95 |
| Badwidth (GHz) | 4 | 4 |
| Beamwidth (o) | 4 | 8 |
| Antenna Gain (dB) | 26 | 24 |
| Sidelobe (dB) | 13 | 3 |
| Cross-Polarization Supression (dB) | 22 | 24 |
| Dimensions (L mm × W mm) | 22.4 × 22.4 | 5.6 × 5.6 |

Embodiments described herein illustrate but do not limit the disclosure. It should also be understood that numerous modifications and variations are possible in accordance with the principles of the present disclosure. Accordingly, the scope of the disclosure is best defined only by the following claims.

What is claimed is:

1. A system comprising:
   a panel of planer antenna arrays, each planer antenna array comprising a plurality of circularly polarized antenna elements in a planar surface, wherein each antenna element includes a spiral plate;
   an array of converters for converting an ultra wide band (UWB) radar signal to V-band or W-band frequency;
   a feed network connecting the V-band or W-band frequency signal to each of the antenna elements; and
   a plurality of amplifiers dispersed in the feed network and configured to provide spatial power combining and beam forming of the V-band or W-band frequency signal for high resolution detection of a tissue anomaly.

2. The system of claim 1, further comprising a signal processor that is configured to:
   measure a path delay between a transmitting antenna and a receiving antenna of the panel via a point in the tissue;
   extract and time-align the spatially beam formed signal from the point; and
   perform image processing using the extracted and time-aligned signal to provide an image presenting the distinct dielectric properties of the tissue anomaly.

3. The system of claim 1, wherein:
   the signal includes a transmitted signal and the amplifiers comprise power amplifiers.

4. The system of claim 1, wherein:
the signal includes a received signal and the amplifiers comprise low noise amplifiers.

5. The system of claim 1, wherein the system includes:
an image processor that combines processing from both right hand circularly polarized (RHCP) reflected signals and left hand circularly polarized (LHCP) reflected signals to provide enhanced edge detection of the tissue anomaly.

6. The system of claim 1, wherein the system includes:
an image processor that analyzes information from both right hand circularly polarized (RHCP) reflected signals and left hand circularly polarized (LHCP) reflected signals to provide phase information for detection of the tissue anomaly.

7. The system of claim 1, wherein:
the signal comprises a pseudo-random coding that allows a correlating receiver to extract very low energy reflected signals from background noise to provide a coding gain.

8. The system of claim 1, wherein:
the panel of planar antenna arrays comprises a linear, 1×n, array to provide enhanced resolution of the cross section of the tissue anomaly.

9. A method for detecting a tissue anomaly in a subject, comprising:
scanning the subject using a spatially beam formed, high resolution radio frequency signal transmitted from a panel of antenna arrays;
measuring a path delay between a transmitting antenna and a receiving antenna of the panel via a point in the tissue anomaly;
extracting and time-aligning the spatially beam formed radio frequency signal from the point; and
performing image processing using the extracted and time-aligned signal to provide an image presenting the distinct dielectric properties of the tissue anomaly.

10. The method of claim 9, wherein scanning further comprises:
transmitting from a first transceiver in an array comprising a plurality of transceivers; and
receiving from all receivers in the plurality of transceivers of the array.

11. The method of claim 9, further comprising:
performing the scanning in a single exposure without mechanical movement of the panel relative to the subject during the scanning.

12. The method of claim 9, further comprising:
performing spatial power combining and beam forming of the transmitted signals via a plurality of power amplifiers dispersed in the feed network.

13. The method of claim 9, further comprising:
performing spatial power combining and beam forming of the received signals via a plurality of low noise amplifiers dispersed in the feed network.

14. The method of claim 9, further comprising:
scanning using the spatially beam formed radio frequency signal comprising an ultra wide band (UWB) pulse for detecting differences in permittivity of the subject and the tissue anomaly.

15. The method of claim 9, further comprising:
performing spatial power combining and beam forming from an antenna array comprising alternating right-hand circularly polarized (RHCP) and left-hand circularly polarized (LHCP) for enhanced edge detection of the tissue anomaly.

16. The method of claim 9, further comprising:
analyzing information from both right hand circularly polarized (RHCP) reflected signals and left hand circularly polarized (LHCP) reflected signals to provide phase information for detection of the tissue anomaly.

17. The method of claim 9, wherein:
the panel of antenna arrays comprises a linear, 1×n, array to provide enhanced resolution of the cross section of the tissue anomaly.

18. The method of claim 9, wherein scanning comprises transmitting and receiving the radio frequency signal in the V-band or the W-band for enhanced resolution of the tissue anomaly.

19. The method of claim 9, wherein:
the signal comprises a pseudo-random coding that allows a correlating receiver to extract very low energy reflected signals from background noise to provide a coding gain.

* * * * *

UNITED STATES PATENT AND TRADEMARK OFFICE
CERTIFICATE OF CORRECTION

| | |
|---|---|
| PATENT NO. | : 9,372,256 B2 |
| APPLICATION NO. | : 14/191118 |
| DATED | : June 21, 2016 |
| INVENTOR(S) | : Farrokh Mohamadi |

It is certified that error appears in the above-identified patent and that said Letters Patent is hereby corrected as shown below:

In the specification

In Column 5, Line 64, change "6" to --16--.

In Column 10, Line 29, change "Badwidth" to --Bandwidth--.

In Column 10, Line 33, change "Supression" to --Suppression--.

Signed and Sealed this
Twenty-third Day of August, 2016

Michelle K. Lee
*Director of the United States Patent and Trademark Office*